United States Patent [19]

Amoils

[11] Patent Number: 4,857,047
[45] Date of Patent: Aug. 15, 1989

[54] FINGER OPERATED VACUUM BYPASS SUCTION HANDPIECE/HOLDER APPARATUS FOR OCULAR CORTEX ASPIRATION AND REFLUXING

[76] Inventor: Selig P. Amoils, 1202 Medical Arts, Jeppe Street, Johannesburg, South Africa

[21] Appl. No.: 142,681

[22] Filed: Jan. 11, 1988

[30] Foreign Application Priority Data

Jan. 27, 1987 [ZA] South Africa ............... 87/0575

[51] Int. Cl.$^4$ .............................................. A61M 1/00
[52] U.S. Cl. ...................................... 604/30; 604/119; 604/902
[58] Field of Search ................ 604/118, 119, 902, 30, 604/35, 36; 433/91; 15/407, 408

[56] References Cited

U.S. PATENT DOCUMENTS

| 3,610,242 | 10/1971 | Sheridan et al. ............... 604/119 |
| 4,299,221 | 11/1981 | Phillips et al. ................ 604/30 |
| 4,397,640 | 8/1983 | Storz ............................ 604/35 |

FOREIGN PATENT DOCUMENTS 1491755 12/1966 Fed. Rep. of Germany ...... 604/902

OTHER PUBLICATIONS

Cilco, Inc.; "The I/A System 2000", 1985.
Advertisement of Mentor–O&O, Inc.; "Argus Annual Meeting Edition"; p. 16; Nov. 11, 1987.
Bulletin Sheet of CooperVision, "The Cavitron/Kelman Model 6500, etc."; 1987.
"Bacterial Recovery from Automated Cataract Surgical Equipment", Henry M. Clayman et al., J. Cataract Refract. Surg., vol. 12, 1986, pp. 158–161.
Flier of Visitec Company, "Visitec for all the Right Reasons", 1987.
"New Coaxial System for Manual Extracapsular Cataract Surgery"; Robert N. Fabricant et al.; AM Intraocular Implant Society Journal, vol. 11, Sep. 1985, pp. 493–494.

*Primary Examiner*—Jerome L. Kruter
*Attorney, Agent, or Firm*—Rines and Rines; Shapiro and Shapiro

[57] ABSTRACT

A novel finger-actuated bypass holder apparatus for ocular cortex fluid aspiration and refluxing and the like, in which the vacuum or suction is normally bypassed through an aperture in the holder which the surgeon may, at will, occlude or open with the finger to enable instantaneous application or removal of vacuum and fine control of aspiration, and with a forward proximal squeezable reflux chamber also finger-actuable at the operating site.

10 Claims, 2 Drawing Sheets

FINGER OPERATED VACUUM BYPASS SUCTION HANDPIECE/HOLDER APPARATUS FOR OCULAR CORTEX ASPIRATION AND REFLUXING

BACKGROUND OF THE INVENTION

The present invention relates to apparatus for accurately aspirating the ocular contents during surgery, including aspiration of the opaque crystalline lens cortex, and for enabling refluxing of the same, as well as aspirating vitreous gel and similar applications, being more particularly directed to improved finger-actuated vacuum-control apparatus for effectuating the same.

In previous apparatus of this character, using peristaltic or diaphragm pump vacuum sources, foot switch control of the aspirating or vacuum application and removal has been universally employed and considered necessary, as described, for example, in a 1985 bulletin of Cilco, Inc. entitled "The I/A System 2000"; and advertisement of Mentor-0&0, Inc., appearing on page 16 of Argus Annual Meeting Edition, Nov. 11, 1987; a 1987 bulletin sheet of CooperVision, "The Cavitron/Kelman Model 6500, etc.", more fully described in "Bacterial recovery from automated cataract surgical equipment", by Henry M. Clayman, et al., appearing in *J. Cataract Refract Surg.*, Vol. 12, March, 1986, pages 158-161; and a 1987 flier of Visitec Company entitled "Visitec for all the right reasons". All these machines have had to use a foot switch to control the vacuum. In other words, to relieve the vacuum, the surgeon takes the foot off the foot switch and the pump stops. A method then has to be employed to relieve the vacuum in the line. One of the important problems with this is that the air passes through the console itself and bacterial contamination can result, as described in said Clayman et al. article. Such foot-pedal control, thus, leaves much to be desired in the sensitivity of control, the distraction of the surgeon from the operating site, the bacterial problems in vacuum relief as described in the said Clayman et al. article, and generally the lack of variable vacuum control—either set at irrigation minimum or maximum, among other limitations.

SUMMARY OF THE INVENTION

An object of the present invention, accordingly, is to provide a new and improved surgical aspiration/irrigation control apparatus of such character that not only completely obviates the necessity for cumbersome foot-pedal vacuum cut-off and application and its disadvantages above delineated, but substitutes novel instantaneous and more sensitive finger control of continuously supplied vacuum, and further enables finger squeezing of a proximal fluid refluxing chamber right at the cannula region of the operation, all without any of the above-mentioned or other limitations of the prior art.

Other and further objects will be explained hereinafter and are more particularly delineated in the appended claims.

In summary, from one of its broader aspects, the invention embodies a suction-operated aspiration apparatus as for withdrawing opaque crystalline lens cortex and the like through a cannula inserted into the eyeball, a finger-operated vacuum bypass suction handpiece having, in combination, a pair of flexible tubes, one being adapted for connection at one end to a continuously operable vacuum or suction source and at its other end to a vacuum bypass aperture in the handpiece that may be finger covered to control the bypass; and the other tube, of diameter much smaller than that of the said one tube and also open to said vacuum source and extending past the bypass at its other end to said aspiration cannula. The construction may involve double or coaxial tubing leading from the vacuum source to the bypass aperture of the handle or handpiece held in the surgeon's fingers. The said one tubing leads directly to the vacuum source of the much smaller diameter other tubing. If the surgeon leaves the handle aperture uncovered, the vacuum is bled through the one tubing to atmosphere with no vacuum force exerted on the other tubing which is directly connected to the fixed and detachable cannula to be inserted into the eyeball. By occluding the handle aperture with a finger, the surgeon can build up vacuum in the tubing and cannula slowly or very rapidly, as well as, more importantly, relieving the vacuum in the cannula with great speed and precision. Proximal flexible reflux chamber facility is also provided; and other preferred and best mode details of construction are later presented.

BRIEF DESCRIPTION OF THE DRAWINGS

The invention will now be described with reference to the accompanying drawings, FIG. 1 of which is a longitudinal partly sectionalized view of a preferred embodiment of the invention.

DESCRIPTION OF THE PREFERRED EMBODIMENTS

Figure 1:
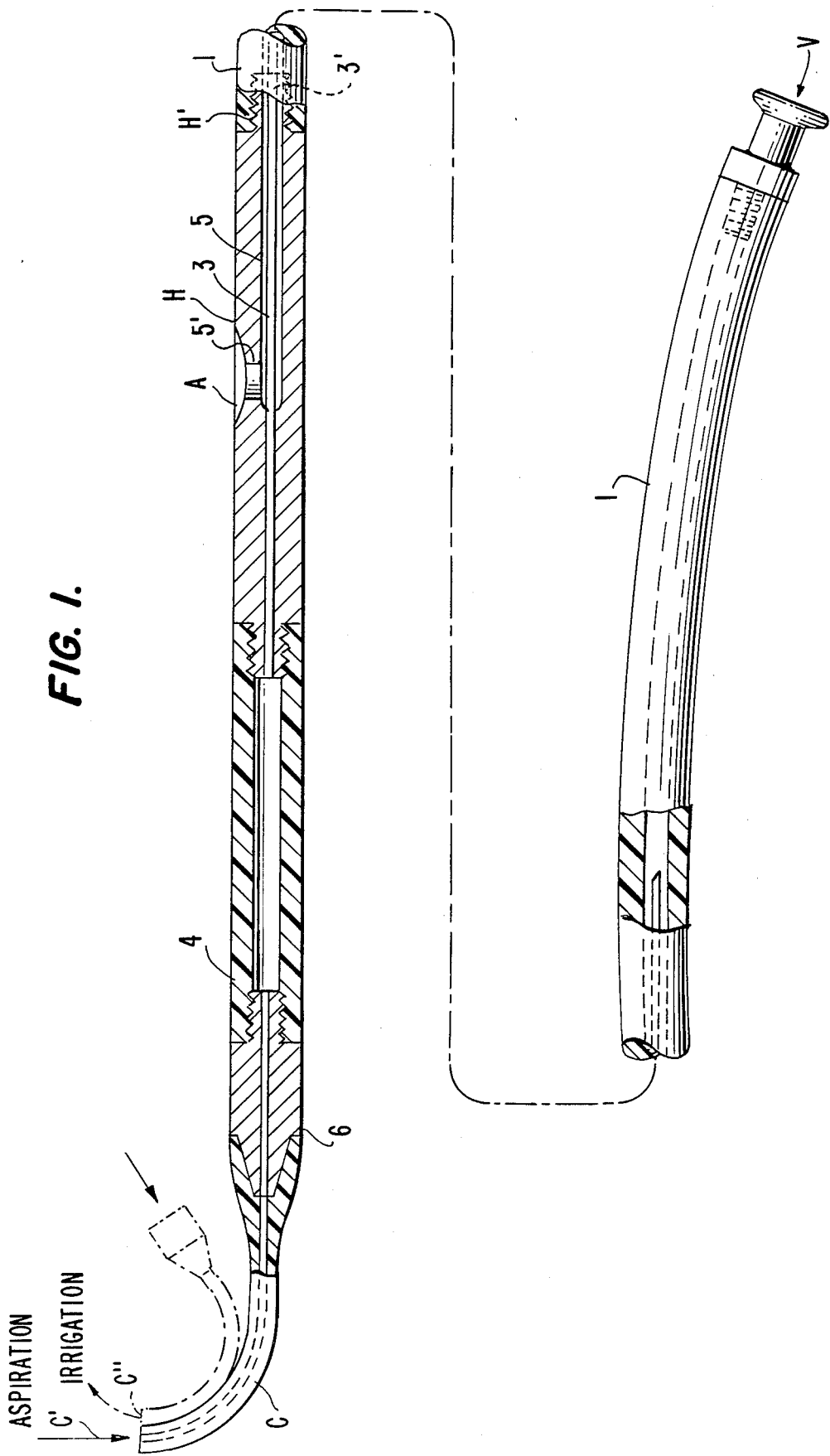
Figure 2:
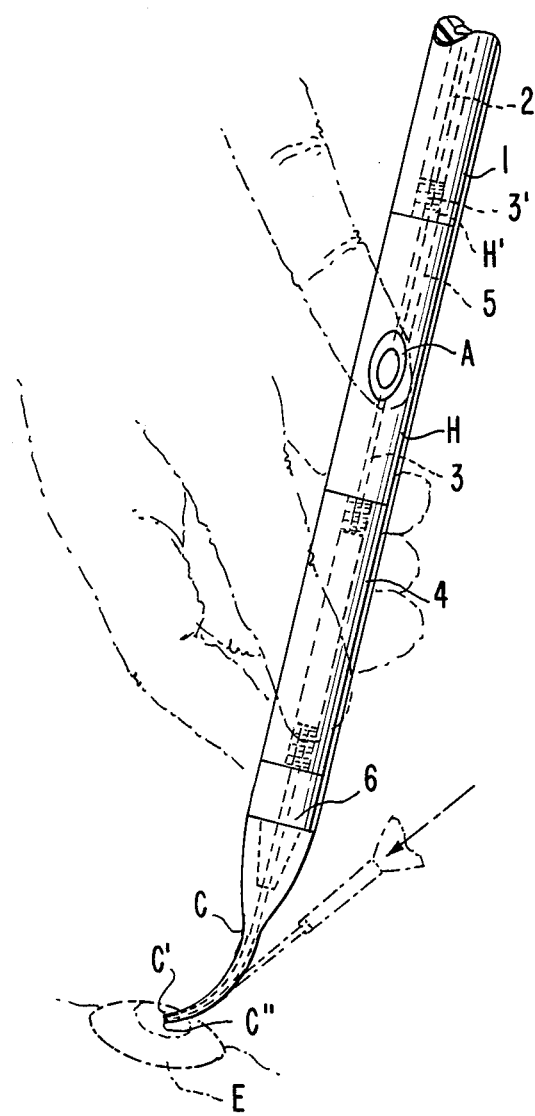
FIG. 2 is a similar fragmentary view illustrating the use of the surgical instrument.

Referring to FIG. 1, a flexible tubing 1, as of silicone rubber or the like, is shown extending from a vacuum or suction source V, preferably of the diaphragm or piston suction pump types, to an aspiration-irrigation double cannula C (as described in said Visitec and other articles) for withdrawing opaque crystalline lens cortex material and the like through the cannula when inserted by the surgeon in the eyeball E, FIG. 2, and providing irrigation fluid, as needed, the suction aspiration orifice being shown as C', and the irrigation orifice at C". A cylindrical handpiece or handle H, as of stainless steel or TEFLON TM type plastic or the like, is inserted in-line into the tubing 1 near the cannula end, connecting left and right-hand sections of the tubing. The handpiece H has a longitudinally axially extending inner passage 3, illustrated in the form of a hollow needle, coaxially surrounded over its right-hand portion by a parallel passage 5 that, intermediate the handpiece H, laterally or transversely communicates at outlet 5' with an external aperture A serving normally as a vacuum bypass aperture, later more fully described, and adapted to be covered by the surgeon's finger, FIG. 2, for suction application to enable aspiration operation and control.

In the coaxial version of FIG. 1, the flexible tubing 1 to the right of the handle H thus is connected at its right-hand end to the continuously operating vacuum source V, and through internal handle passage 5, which is almost the diameter of the hollow passage of tubing 1 (resiliently fitted over the right-hand reduced-diameter terminal section H' of the handle) to the external vacuum bypass aperture A intermediate the handle. In inner flexible tubing 2 of inner diameter selected to be small compared to that of the inner diameter of tubing 1 and of the passage 5, is shown extending to the right of the handpiece H longitudinally coaxially or near-coaxially within the outer tubing 1 and considerably shorter than tubing 1 that connects to the vacuum source V, being open at its right-hand end to the vacuum withint tubing 1 as derived from source V and fitted at its left-hand end over a protruding terminal section 3' of the inner passage or needle 3. This enables the inner tubing 2 to communicate through inner similarly small diameter passage 3 to a flexible tubular section 4 of tubing 1, serving as a later-described proximal squeezable fluid-refluxing chamber, and thence through a tapered fitting 6 to the aspiration channel of the cannula C.

This construction provides a uniform diameter tubular apparatus 1-H-4-6, the cannula end of which is flexibly manipulatable by the surgeon's hands, applying the finger of one hand to cover or open aperture A, FIG. 2, holding handpiece H, and also to squeeze the reflux chamber 4 with the fingers of the other hand. In operation, the surgeon, holding the handle H and cannula fitting 6, applies the cannula to the eye. Because of the much smaller diameter of the vacuum-application passageway 2-3 compared to the bypass passageway 1-5-A, through the vacuum pump or source V is continuously on, no suction normally is applied to the cannula opening C', the vacuum being bypassed through aperture A. By applying a finger to cover aperture A, the surgeon instantaneously applies the vacuum to the cannula and equally instantaneously cuts off the suction and effects instantaneous release by removing the finger to re-open aperture A—a very sensitive and highly controllable technique, and controlled right at the site of the operation by the surgeon's hands, alone. The elimination of the requirement for vacuum source shut-off and turn-on and for foot switch control also obviates the disadvantages of delving beneath the operating table and the problem of the foot pedal slipping away and out of position, requiring attention to be focused away from the operating probe. The finger control, moreover, is very much lighter and quicker and more delicate than foot control and enables the vacuum source to be continuously operative. Another factor which is very important in the machine of the invention is that, because of its very simple basic design, a little bleed valve may readily be incorporated into the console to set the maximum level of the vacuum, such as 150 mm, 200 mm, 300 mm, 350 mm, or maybe 400 mm of mercury. Now, even if the fingertip is occluded, it is impossible for the vacuum level to go higher than the present level. It can go lower, but it cannot exceed the set level, as contrasted with machines such as the before-mentioned Cavitron or VISITEC TM apparatus, and this allows the surgeon to determine the level at which the surgeon would like to operate; for example, 250 mm suction or 200 mm suction or 300 mm suction—and this is a very simple control in a very inexpensive unit.

With the forward squeezable refluxing chamber 4 immediately adjacent the cannula, moreover, the surgeon readily instantaneously releases vacuum and moves the finger of an operating hand to control refluxing of fluid. Toward this end, the flexible "squeegee" chamber 4 that is forwardly placed between the vacuum bypass handle H and the fitting 6 which attaches the irrigation-aspiration double canulla C, is made long enough so that is can facilely be squeezed between two fingers and cause instantaneous reflux into the anterior chamber, and also release any aspirated anterior capsule which has been sucked into the orifice and so prevent tearing of the anterior capsule and damage to the vitreous face. This is an extremely important factor and also allows the instrument handle, flexibly fitted within tubing 1, to be maneuvered and flexed over the patient's brow and to be rotated with great facility. This is totally different from prior art reflux systems, such as used by the before-mentioned Visitec machine (which also requires foot pedal operation), where the reflux bulb is proximal to the probe handle and the hand has to be moved to squeeze it. During the time it is squeezed, moreover, the outlet hole has to be covered as well.

A typical successful experimental operating system of the type described in connection with FIGS. 1 and 2 employed an outer vacuum bypass silicone tubing 1 having an outer diameter of 8 mm and an inner diameter of 5 mm and a length of about 1.6 meters. The smaller diameter vacuum tubing 2 was 75 cm in length with an outer diameter of 2 mm and an inner diameter of 1 mm—providing much greater resistance (the outer tubing being thus of the order of 5 times greater diameter or 25 times greater cross-sectional area). The length of the effective reflux tubing section 4 was about 3 cm (being a section of the tubing 1) and the exposed body of the handpiece or holder H about 2 cm with an effective aperture A of about 4-5 mm. Clearly the passages 3, 5, etc. in the handpiece H may be integrally formed in commercial apparatus. Another important advantage is that should the fitting to the vacuum system (shown as a conventional BD lock fitting in FIG. 1 at far right) be inadvertently not tightened, there is no buildup of vacuum when the finger is placed on the vacuum bypass handpiece H, and the surgeon will immediately notice a reduced reading in the pressure.

The invention thus provides a substantial advantage in enabling vacuum finger control without any need for foot switches, as in prior art systems.

Still another important advantage of the invention resides in the fact that with other machines which use a vacuum release system, such as the before-mentioned Cavitron irrigation/aspiration device, in order to relieve the vacuum between a peristaltic pump and the handpiece, a solenoid valve must be opened to allow for air to be sucked into the pipe. As before explained, this air is passed through contaminated workings inside the console and causes bacterial contamination of the system, requiring filtering. This contamination cannot occur with the vacuum bypass handpiece of the invention since the entire handpiece and tubing is sterilized by autoclaving with every new case or is disposable, and there is no bypass passable through the console, and this is a very important safety feature, especially in the United States.

The flexible construction of the invention allows a much easier rotation of the irrigation/aspiration cannula C, and this allows the cortex to be aspirated at the twelve o'clock position with greater ease and also at the three o'clock and the nine o'clock positions by means of rotation of the needle. The instrument can be used in slightly different ways, either concentrating the grip on the taper fitting 6 or on the handle H, and rotation of the needle can be caused by rotating the handpiece H, or else the fitting 6. This obviously would depend upon the surgeon's preference and skills.

The present invention, furthermore, provides for the first time in a mechanical pump vacuum system the advantages of hand-held or manual syringe techniques as in the Simcoe technique, wherein the surgeon may aspirate by pushing the syringe up with the thumb and, if unwanted material is obtained, causing refluxing by putting the thumb on the top of the syringe and squeezing it. (See, for example, "New coaxial system for manual extracapsular cataract surgery", Robert N. Fabricant and Ronald Cangemi, *AM Intraocular Implant Society Journal*, Vol. 11, September, 1985, pages 493–4.) Now this kind of hand control flexibility can be achieved in a vacuum pump apparatus with the present invention.

The invention, moreover, enables variable vacuum control by means of, for example, a regulator which allows a variable bleed before the vacuum end enters tubing 1. One can also get some degree of vacuum control by means of partial finger-covering of the bypass aperture A. It must be remembered, however, that when the finger is removed from the bypass aperture A, within a fraction of a second, the vacuum is gone because of the much larger diameter of the bypass tubing 1 than the suction or vacuum line 2–3.

Figure 3:
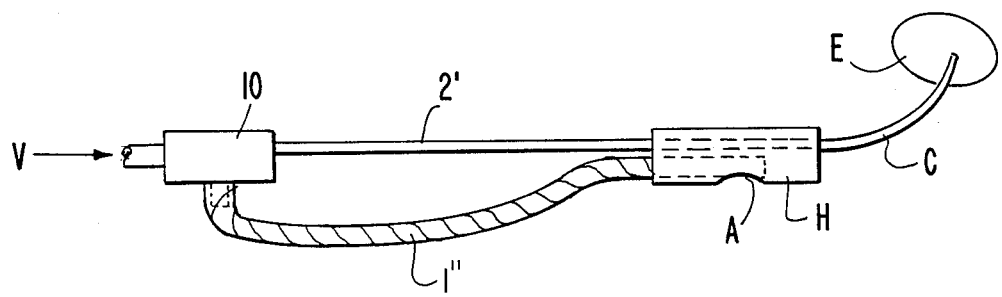
FIG. 3 is a similar view of a modification.

While the apparatus of FIGS. 1 and 2 shows the small diameter tubing 2 disposed within and somewhat coaxially with the outer tubing 1, having the advantages of a unitary system and the shorter length of tubing 2, if desired, as before mentioned a double-tubing construction may be employed as in FIG. 3, wherein the larger-diameter tubing 1" extends coextensively or side-by-side with the vacuum application line 2' from a common plenum chamber 10 connected to the vacuum source V.

Further modifications will also occur to those skilled in this art, such being considered to fall within the spirit and scope of the invention as defined in the appended claims.

What is claimed is:

1. In a suction-operated aspiration apparatus as for withdrawing opaque crystalline lens cortex and the like through a cannula inserted into the eyeball, a finger-operated bypass suction handpiece having, in combination, a pair of tubes at least one of which is flexible, said one tube being in fluid communication at one end with a continuously operable suction source and being in fluid communication at its other end with a bypass aperture in the handpiece that may be finger covered to control the bypass, the other tube being of diameter much smaller than that of the said one tube and extending past the bypass and being in fluid communication at one end with said suction source at its other end with said aspiration cannula by way of a squeezable reflux chamber means connected between the handpiece and said aspiration cannula to control refluxing.

2. A finger-operated bypass suction handpiece as claimed in claim 1 and in which said other tube is at least partially substantially coaxially disposed within said one tube.

3. A finger-operated bypass suction handpiece as claimed in claim 1 and in which said other tube extends within said one tube a shorter distance toward the vacuum source than the said one tube.

4. A finger-operated bypass suction handpiece as claimed in claim 1 and in which said tubes are substantially coextensive between said suction source and said handpiece.

5. In a suction-operated aspiration apparatus as for withdrawing opaque crystalline lens cortex and the like through a cannula inserted into the eyeball, a finger-operated bypass suction handpiece having, in combination, inner and outer substantially coaxially extending tubes, the outer tube being flexible and in fluid communication at one end with a continuously operable suction source and at its other end with a bypass aperture that may be finger covered to control the bypass, the inner tube being in fluid communication at one end with the outer tube and extending past the bypass aperture and at its other end into a flexible chamber means communicating to said aspiration cannula, the flexible chamber means being squeezable to permit a surgeon to control the refluxing of fluid after the suction has been removed from the cannula by uncovering said aperture.

6. A finger-operated bypass suction handpiece as claimed in claim 5 and in which the inner tube is shorter than the outer tube and terminates within the outer tube a distance from the bypass aperture relatively short compared with the length of the outer tube to its suction source connection.

7. A finger-operated bypass suction handpiece as claimed in claim 5 and in which the said other end of the outer tube connects with an in-line tubular connector handle having coaxial tubular passages, the outer of which is provided with a laterally communicating external outlet terminating intermediate the handle in the bypass aperture, and the inner tubular passage of which constitutes at least part of said inner tube and is connected at one end with said flexible chamber.

8. A finger-operated bypass suction handpiece as claimed in claim 7 and in which said inner tube includes a flexible tubular member fitted over an end of said inner tubular passage protruding axially beyond and from the handle, and said outer tubular passage of the handle coaxially surrounds and communicates internally and intermediately of the handle with said bypass aperture.

9. A finger-operated bypass suction handpiece as claimed in claim 8 and in which the coaxially surrounding outer tubular passage has an end portion formed in a terminal section of the handle which is of reduced diameter to receive said other end of the outer tube such that the outer tube and intermediate portion of the handle are in-line in a continuous substantially uniform diameter tubular apparatus.

10. A finger-operated bypass suction handpiece as claimed in claim 9 and in which said flexible chamber is of substantially said uniform diameter and fits in-line over a similar reduced diameter section at the other end of the handle.

* * * * *